United States Patent [19]

Hsia et al.

[11] 4,223,004

[45] Sep. 16, 1980

[54] DRUG COMPOSITIONS

[75] Inventors: Jen C. Hsia, Don Mills; Arthur E. Le Blanc, Toronto; Joan A. Marshman, Agincourt, all of Canada

[73] Assignee: The Governing Council of the University of Toronto, Toronto, Canada

[21] Appl. No.: 799,309

[22] Filed: May 23, 1977

[30] Foreign Application Priority Data

May 24, 1976 [GB] United Kingdom ............... 21443/76

[51] Int. Cl.² ..................... A61K 29/00; G01N 33/16
[52] U.S. Cl. ......................................... 424/9; 128/1.1; 23/230 B; 424/1.5; 424/12
[58] Field of Search .......................... 424/1, 9, 12, 1.5; 128/1.1; 23/230 B

[56] References Cited

U.S. PATENT DOCUMENTS

| | | | |
|---|---|---|---|
| 3,275,416 | 9/1966 | Zaar et al. | 23/230 B |
| 3,847,138 | 11/1974 | Gollub | 128/1.1 |
| 3,867,366 | 2/1975 | Rubenstein et al. | 424/1 |
| 3,873,270 | 3/1975 | Hamilton et al. | 23/230 B |
| 3,901,655 | 8/1975 | Skukla et al. | 23/230 B |
| 3,915,639 | 10/1975 | Friedenberg | 23/230 B |
| 3,993,741 | 11/1976 | Otto | 424/1 |
| 4,022,876 | 5/1977 | Anbar | 424/1 |
| 4,036,823 | 7/1977 | Soares | 424/1 |
| 4,049,683 | 9/1977 | Okamoto et al. | 424/1 |

*Primary Examiner*—Benjamin R. Padgett
*Assistant Examiner*—Christine M. Nucker
*Attorney, Agent, or Firm*—Ridout & Maybee

[57] ABSTRACT

Monitorable drug compositions contain known proportions by weight of a drug e.g. methadone and an isotopic analogue e.g. deuterated methadone. A urine specimen or blood specimen can be tested to reveal whether the proportion of the two constituents in the urine is the same as the proportion in the composition that was prescribed to the patient. A discrepancy will reveal that the patient has supplemented his dosage with drugs obtained from another source.

17 Claims, 7 Drawing Figures

DRUG COMPOSITIONS

BACKGROUND OF THE INVENTION

1. Field of the Invention

The present invention relates to drug compositions such as narcotic compositions, and also to methods, more especially intended for use in maintenance therapy programs. Maintenance therapy programs, under which the addicted patient receives a prescribed and regulated dosage of a narcotic or like drug under the supervision of a qualified therapist, are considered by many to be a satisfactory and effective treatment strategy for dealing with the problems of drug addiction since they give an opportunity for contact with the addict in a clinical environment in which therapeutic procedures can be applied so as to at least mitigate the social and medical difficulties associated with addiction.

Up to the present time, there has existed the problem of monitoring compliance by the patient with the maintenance program. It has been found that in some instances the patient has supplemented his prescribed dosage from illicit street sources, thus diminishing the effectiveness of the therapy. Further, the patient may illicitly dispose of or divert his dosage to other addicts.

2. Description of the Prior Art

Known analysis techniques can give a qualitative indication of the nature of the drugs taken, or can give a quantitative indication of the concentration of a drug in a specimen, but they do not permit determination of whether a given patient is taking his dosage as prescribed or whether he is supplementing it with the same narcotic obtained illegally. The use of creatinine and like markers does not solve the problem since the excretion profile of these substances in the urine is different from the drugs employed in maintenance programs. In the patent literature there are found descriptions of various techniques employed in connection with testing for drugs, e.g. the method of preparing lyophilized urine described in U.S. Pat. No. 3,901,655, Shukla et al. A method of determining barbiturates in a specimen is referred to in U.S. Pat. No. 3,275,416, Zaar et al. U.S. Pat. No. 3,873,270 discloses a process for determining methadone in a specimen. Such determinations will not however indicate directly whether a patient has supplemented his prescribed dose. U.S. Pat. No. 3,915,639, Friedenberg describes a testing dip stick for abuse-type drugs such as amphetamines, narcotics, and barbiturates. This dip stick could not indicate whether a patient may be supplementing the dosage of a particular drug allotted to him with additional quantities of the same drug obtained illicitly.

SUMMARY OF THE INVENTION

The present invention provides compositions and methods whereby this difficulty may be alleviated and in a first aspect consists in a monitorable drug composition comprising a predetermined weight of a drug, especially a drug liable to illicit abuse together with a predetermined proportion by weight of an isotopically distinct analogue of the drug.

With such compositions as are now provided, the physiological activity, e.g. analgesic activity, therapeutic value, or toxicity of the composition may be substantially identical to that of the unmodified composition, and further the active drug constituents in the mixture may be absorbed, distributed and excreted through the metabolism in the same proportions as those in which they were originally present in the dosage supplied. Since the constituents of the composition are of dissimilar molecular weight, determination of the ratio of the isotopically distinguished constituents in a urine, blood, or other physiological specimen from the patient can be readily carried out by physical analytic methods.

Thus, through analysis, notably by mass spectrographic analysis of a urine specimen from a patient receiving the above labelled composition, it is possible to obtain an indication of non-compliance with the maintenance program, since any discrepancy in the ratio of the constituents over the ratio in the composition supplied will indicate unauthorized supplementing of the prescribed dosage.

Although the application which is of greatest interest is in connection with addictive and other drugs which are liable to illicit abuse, the principles disclosed herein are also applicable in connection with medicinal or other substances having physiological therapeutic, or pharmacological effect, where a practitioner may wish to monitor compliance with a regime of prescribed dosages. As will be appreciated, for all these applications the composition is prepared at a pharmacologically-acceptable standard of purity, and is free from undesired toxic and noxious materials.

DESCRIPTION OF THE PREFERRED EMBODIMENTS

As examples of drugs to which the present invention may be applied, there can be mentioned opiates e.g. morphine and heroin, synthetic opiates, e.g. methadone and acetyl methadol, as well as barbiturates and amphetamines.

Amongst the isotopic analogues that can be used, examples are deuterated compounds, and carbon -13 labelled compounds. Other stable non-radioactive isotopes can also be used as will readily be understood by those skilled in the art.

Various methods are known or can readily be adapted from methods previously used for preparing isotopic analogues of drugs and like compounds.

More specifically, various analogues of methadone deuterated at the 1- and 2-positions can be prepared by reacting a Grignard solution prepared from magnesium and an appropriately deuterated ethyl bromide compound, and exchanging any reactive acidic deuterium atom or atoms at the 2-position with hydrogen by reaction with a dilute alkaline solution.

These reactions can be represented by the following scheme.

Deuterium can be also introduced into the metadone molecule at positions other than those described above. A general approach to compounds of this type is shown in the following scheme. Reference may be made in this connection to an article by Easton, N. R., Gardner, J. H., Stevens, J. S., J. Amer. Chem. Soc. 69, 2941 (1947).

Deuterium atoms may be put on the 5-, 6-, and 7-positions of the methadone molecule by using the appropriate deuterated propene precursors, e.g. tri-deuterated propene-3,3,3,tetra-deuterated propene-2,3,3,3hexa-deuterated propene, and tri-deuterted propene-1,1,2. These procedures can yield deuterated methadones of the following formulae.

A synthetic route for preparing deuterium-labeled morphine is as follows. Acetylation of the morphine analogue obtained will result in the respective heroin derivatives. Reference should be made to an article by Eb- binghaus, N. O. R., Mowat, J. H., Vestogard, P., Kline, N. S., Adv in Biochem. 7 Psychopharmacology, Raven Press (1973) for further details.

Where Me = CD₃, CD₂H or CDH₂

Synthetic routes for the preparation of acetyl methadols are as follows:

Where Ac = —O—C(=O)—CH₃

Synthetic routes for preparing deuterium labeled amphetamines are as follows, using modifications of procedures described by Fentiman, A. F. Foltz, R. L., in J. of Labeled Compounds and Radiopharmaceuticals, Vol XII, No. 1, (1976).

Amphetamine-d₆  Amphetamine-d₅

The above described preparative procedures employ classical reaction steps and can readily be carried out by the skilled chemist. It is known, for purposes other than those of the present invention, to prepare isotopic analogues of drugs, e.g. deuterium-labeled heroin. In the past, such analogues have been employed in assays, wherein a known of the synthetic analogue has been added to a specimen containing an unknown content of the basic, unlabeled, drug so that by the application of physical analytical methods the proportion of unlabeled to labeled material may be determined, whereby the concentration of the unknown drug in the specimen can be derived.

Testing procedures using isotopes have also been used in the analysis of non-pharmacological materials, as for example in the gas phase analysis of carboxylic acids, as described in Smith et al. U.S. Pat. No. 3,859,048.

The said physical analytical methods previously used in the assays referred to above may also be applicable in testing a physiological specimen for the purposes of the invention to determine whether the drug and its isotopic analogue are present in the proportions which are to be expected.

In a practical application of the invention, a plurality of patients to be monitored may each be maintained on an individual distinctive drug composition. Thus, using binary mixtures of normal methadone or other drug and its mono-deuterated analogue, different patients can each be given mixtures containing, say, proportions of 0.9:0.1, 0.8:0.2, 0.7:0.3, etc., by weight, of the normal drug and the analogue. Other patients may be given mixtures containing similarly varying proportions of mono-deuterated and di-deuterated analogues, and other patients can each be given a distinctive ternary mixture and so on.

Periodically, a specimen from each patient can be tested to monitor compliance.

The preferred testing procedure is to subject a purified physiological patient specimen, e.g. urine or blood, to a conventional gas chromatography-mass spectroscopy analysis. Using repetitive mass spectrographic scan, the scan record that is obtained exhibits adjacent bell-shaped outlines representing respectively the unmodified drug and the or each isotopic analogue that is present. The area defined under each curve is a direct measure of the quantity of the respective drug in the specimen. Thus, by comparison of the two areas, the proportions of distinctly labeled constituents can be obtained, and this can then be compared with the proportion that would be expected if the patient has taken only the dosage as prescribed. In this manner any supplementation of the prescribed dose can be revealed.

By using differently labeled compounds, and different proportions of the compounds in the mixture, a wide range of distinguishable drug compositions can be formulated, so that it is possible to give a unique "finger-printed" composition to each patient within at least a selected maintenance program or programs. It will be noted that the labeled compositions need not be supplied to a patient at all times, and that normally an unmodified composition is supplied, and the labeled composition supplied only as a spot check to patients suspected of abuse. In this manner, not only can supplementation be uncovered, but also inter- or intra-program diversion or diversion of a composition into the illicit drug market can be detected through the detection of its characteristic "fingerprint".

By variation of the proportions in which the isotopically distinct constituents are present, of the number of isotopic atoms substituted in the molecule, and by employing various isotopes of the different elements present in the molecule, a large number of distinguishable drug compositions can be formulated as equivalents of any one particular drug. Thus, there exists the possibility of "finger-printing" the respective dosages supplied to patients at least within a selected therapeutic program, or possibly even within a selected geographical area.

Each of the drug constituents in the composition may be isotopically distinct from the unmodified or conventionally available drug, and the composition may comprise more than two distinct constituents.

In the accompanying drawings.

EXAMPLES

Example 1: Preparation of analogue of methadone

A deuterio analogue was prepared for methadone (6-dimethylamino-4,4-diphenyl-3-heptanone) using modifications of preparative procedures proposed by Kleider et al (1945), Report no. 981, Office of Publication Board, Department of Commerce, Washington; Cusic (b 1949), J. Amer. Chem. Soc. 71 3546; and Easton et al (1947) J. Amer. Chem. Soc. 69, 2941.

Firstly, a penta-deutero methadone analogue was obtained by reacting a Grignard solution prepared from magnesium and penta-deuterio ethyl bromide with dl-$\Delta$-dimethylamino-$\alpha,\alpha$-diphenyl-valeronitrile, using deuterium-substituted ethyl bromide obtained from Merck, Sharp and Dohme of Montreal, of isotopic purity greater than 99%. For the sake of simplicity and convenience in the subsequent mass spectrographic investigation, the pentra-deuterio methadone compound obtained was then converted to a tri-deuterio methadone, which has molecular weight close to the unlabeled methadone, and is therefore more readily comparable with the unlabeled material.

Figure 1A:
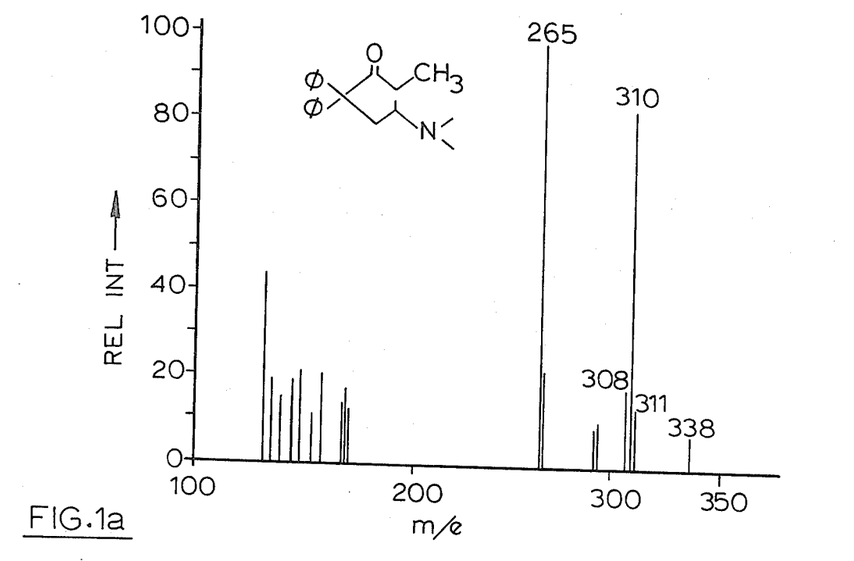
FIGS. 1a and b are plots of chemical ionization mass spectra of methadone and a deuterated analogue of methadone, respectively.
Figure 1B:
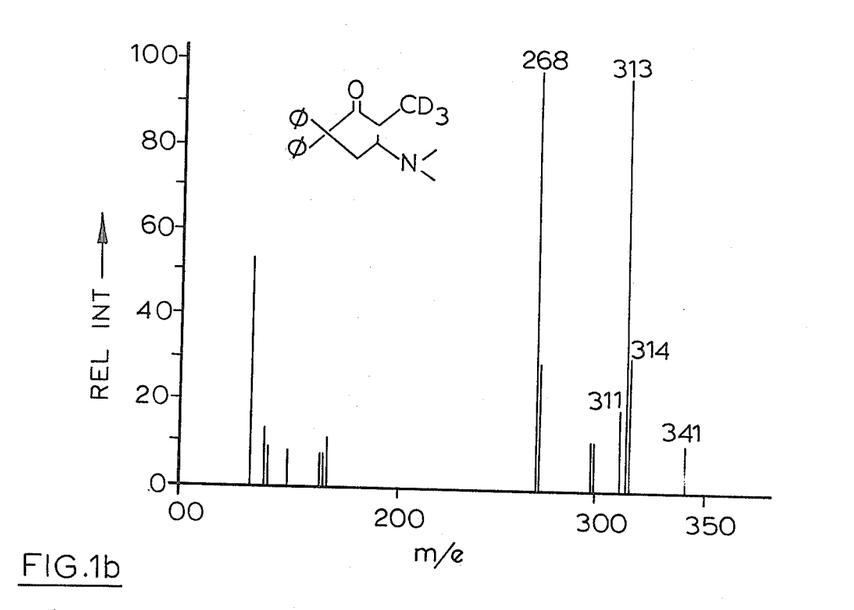
Figure 2:
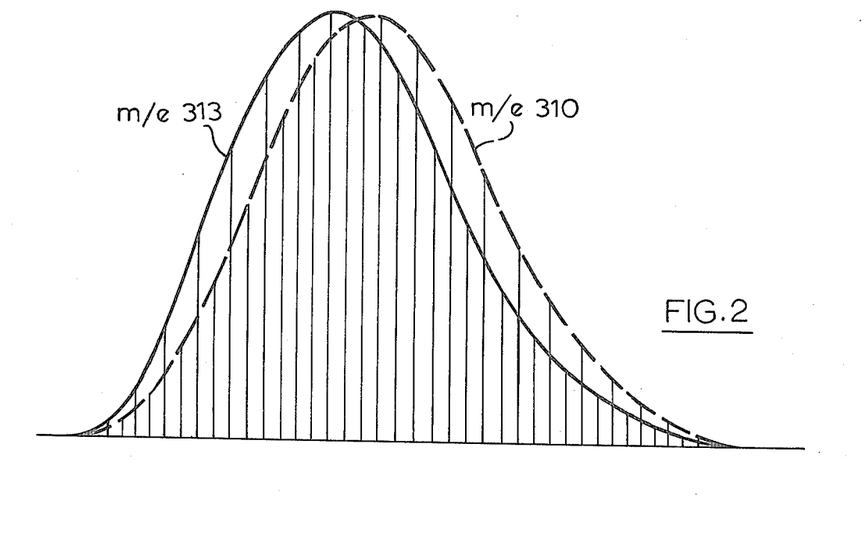
FIG. 2 shows a plot of mass spectrographic repetitive scan record applied to a physiological specimen containing both methadone and the said analogue.

The conversion to the tri-deuterio compound was achieved by exchanging the two acidic deuterium atoms at the 2-position in dilute aqueous sodium hydroxide. The 1,1,1-trideuterio compound obtained (hereinafter referred to as methadone-$d_3$) was found to be analytically pure. The chemical ionization mass spectra of conventional methadone and of the methadone-$d_3$ are shown in FIGS. 1a and 1b.

Example 2: Animal Experiments

The analgesic activities and toxicities of compositions comprising methadone, methadone-$d_3$, and their 1:1 mixture were investigated.

In the investigation of analgesic activity, 0.5 ml intraperitoneal injections were administered to mice, employing varying amounts of the respective compositions in 0.9% NaCl solution, ranging from 3.5 to 13 mg per kilogram body weight, the drug concentrations being expressed in terms of the hydrochloride salt. The analgesic activities were measured as elevation of pain threshold by the hot plate method (55°). The analgesic activities of the three compositions were found to be indentical.

In the investigation of toxicity, intraperitoneal injections were formulated and administered to mice as described above, except that the dosages were in the range of 20 to 65 mg per kilogram body weight. The relative toxicities were determined by comparing the acute mortality with 24 hours. The toxicities of all three preparations were found to be substantially the same, at $LD_{50}$ 41±0.5 mg/kg.

The pharmacokinetics of methadone and methadone-$d_3$ were investigated.

Three rats each received a subcutaneous 0.2 ml injection of a 1:1 mixture of methadone-$d_3$ and methadone at a dosage of 10 mg/kg made up in 0.9% saline. After three hours, the rats were sacrificed and body tissues and urine were isolated. Unchanged methadone-$d_3$ and methadone in the specimens obtained were extracted with organic solvents employing a procedure proposed by Rickards et al (1958) J. Pharmacol. 98, 380.

Each extract was purified by thin layer chromatography using two solvent systems, namely firstly chloroform, and secondly a mixture of ethyl acetate, n-butanol, ethanol, and ammonium hydroxide in 70:10:15:1 ratio.

The purified extracts obtained were then analyzed by a gas chromatography and mass spectroscopy procedure, in which the purified extract was first separated on a 6 ft., 3% SE-30-Chromasorb-W column at 235°. It was determined that the retention times for the methadone-$d_3$ and methadone after injection of the drug mixture into the column were 2 mins 20 secs and 2 mins 21.5 secs, respectively, and the outflow from the column within the appropriate period was then subjected to mass spectroscopy on a Biospect mass spectrometer using repetitive scan in the range m/e 306 to 315.

Figure 3:
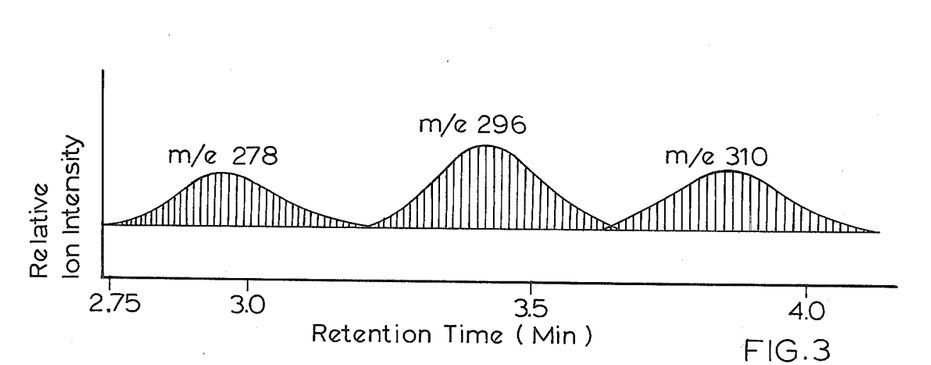
FIG. 3 shows a plot similar to FIG. 2 for a specimen containing methadone, its metabolite, and an external standard compound.

A scan record as shown in FIG. 3 was obtained, wherein the spectral lines represent cumulative ion currents for mass fragments. The record exhibits two distinct bell-shaped outlines, which in FIG. 3 have been graphed in solid and broken lines, respectively, the two outlines peaking at m/e 313 for the methadone-$d_3$ and m/e 310 for the unmodified methadone.

The areas defined under the two curves, which were integrated manually using a planometer, are a direct measure of the ratio of methadone-$d_3$ to methadone in the specimen.

In order to eliminate any errors arising from any impurities contributed from the gas chromatography column, or from variations in the characteristics of the spectrometer, a sample of the dosage administered may be run through the column and the spectrometer immediately after or before the examination of the physiological specimen, and the two results compared.

It was found that with each of the three experimental rats, the ratio of the two components in each specimen was substantially the same as the ratio in the dosage administered.

The results indicated that methadone-$d_3$ has the same rate of absorption, distribution and excretion as methadone, and hence that the proportions of the isotopically distinct components are not altered by passage through the metabolism.

Example 3: Human Trials

Figure 4:
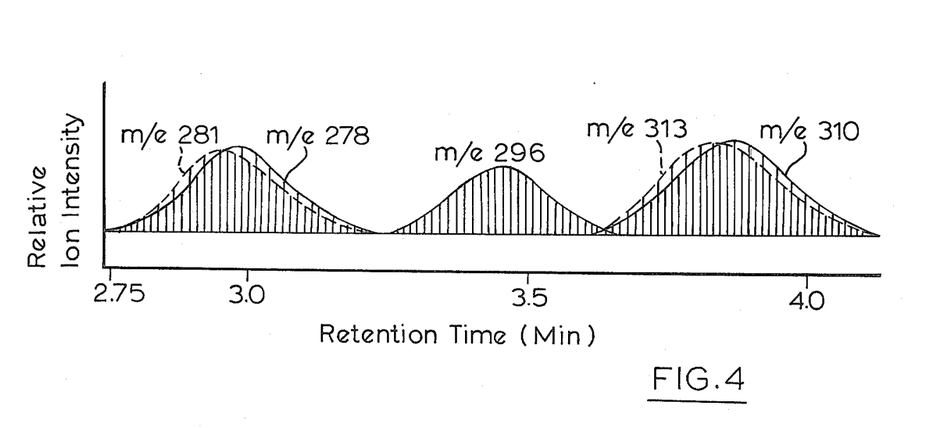
FIG. 4 is a plot for a specimen similar to that of FIG. 3, but including a deuterated analogue of methadone, and its metabolite.
Figure 5:
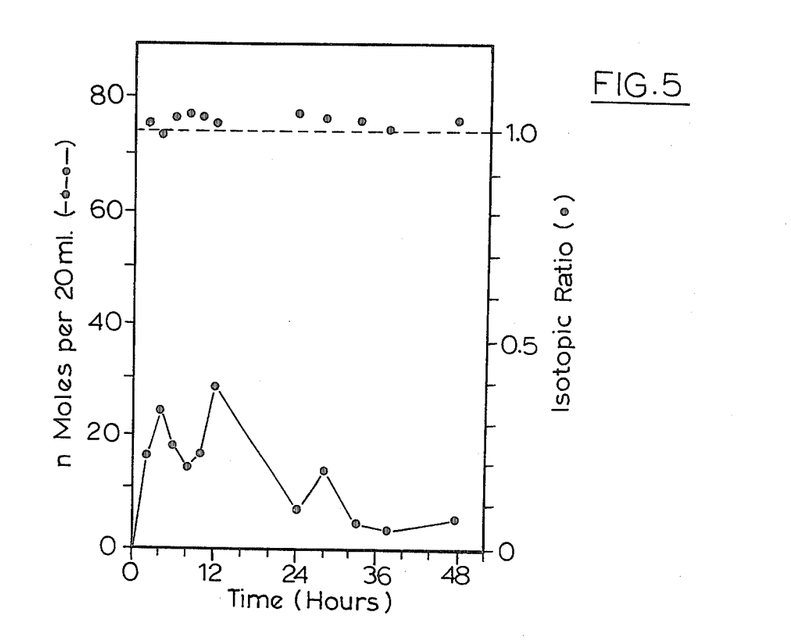
FIGS. 5 and 6 are plots against time of urine levels of drugs and of the ratios of isotopically distinct constituents.
Figure 6:
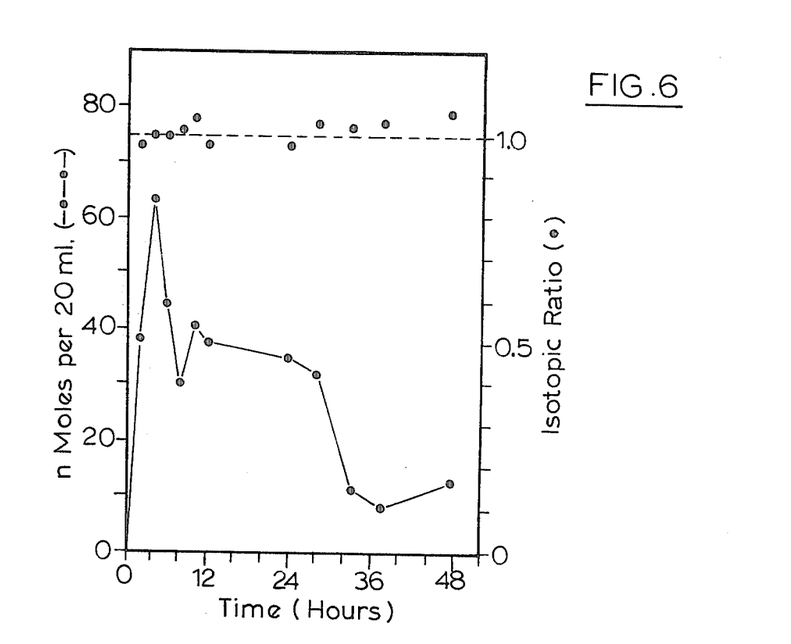

For naive human subjects, the maximum dose of methadone for analgesic purposes is approximately 15 mg/individual. In practice, for the treatment of an opiate habit, the initial requirement of methadone would be much higher. Using the technique of gas chromatography-mass spectroscopy (GC-MS) described in Example 2, the urine levels of unchanged and methadone of its metabolite, 2-ethylidene-1, 5-dimethyl-3, 3-diphenyl pyrrolidine, were measured in six healthy male volunteers taking 5 mg each of methadone and methadone-$d_3$. The amount of metabolite and unchanged drug present were quantitated using a methylketone analogue of methadone as an external standard. FIG. 3 shows the GC-MS tracing of the standard mixture of the pyrrolidine metabolite of methadone (m/e 278), methyl ketone analogue of methadone (m/e 296) and methadone (m/e 310). FIG. 4 is a tracing of urine extract of a subject taking a 1:1 mixture of methadone and methadone-$d_3$. Both the metabolite (m/e 281 and 278) and methadone (m/e 313 and 310) appear as doublets while the external standard (m/e 296) appears as a singlet. FIG. 5 shows the time dependent changes in urine levels of the unchanged methadone, methadone-$d_3$ and their isotopic ratios and FIG. 6 shows the time dependent changes in urine levels of the pyrrolidine metabolite of methadone, methadone-$d_3$ and their isotopic ratios. The urine levels of the labeled and unlabeled drugs and their metabolites were determined by mass fragmentography using 2-dimethylamino-4,4-diphenyl-5-hexanone (m/e 296) as an internal standard. The labeled versus unlabeled drug and metabolite ratios were determined as the ratios of the cumulative ion current of mass fragments 310 (methadone) to 313 (methadone-$d_3$) and 278 (metabolite) to 281 (metabolite-$d_3$) on a Biospect mass spectrometer using methane as the ionization gas. The drugs and metabolites were separated on a 3%-OV-17 column at 235°. The observed peak area ratios of m/e 310 to m/e 296, m/e 313 to m/e 296, m/e 278 to m/e 296 and m/e 281 to m/e 296 were measured by a planimeter. Quantitation of the drug and metabolite levels in urine was achieved utilizing these experimental ratios and a standard curve constructed from ratios obtained by GC-MS assay of urine samples containing known concentrations of methadone (1.43 ug-7.63 ug) methadone (1.39 ug-7.47 ug) methadone metabolite and of the internal standard 4.985 ug). As indicated in FIGS. 5 and 6, although the urinary level of methadone and its metabolite may vary considerably during a two day period, their isotopic ratio may remain unchanged. Results from five subjects are shown in Table 1.

Table 1

| | Renel Excretion of Methadone, Methadone-$d_3$ and their Major Metabolites in Man | | | | | |
|---|---|---|---|---|---|---|
| Subject | Methadone nmole/20 ml | Methadone-$d_3$ nmole/20 ml | Methadone-$d_3$ Methadone | Metabolite nmole/20 ml | Metabolite-$d_3$ nmole/20 ml | Metabolite-$d_3$ Metabolite |
| H.M. | 26.66 (10.75) | 25.78 (10.31) | 1.01 (1.00) | 133.97 (55.83) | 124.99 (52.05) | 0.98 (0.98) |
| R.C. | 3.40 (7.79) | 3.22 (7.46) | 0.99 (1.01) | 40.26 (58.36) | 37.88 (54.71) | 0.99 (0.99) |
| P.A. | 33.79 (15.79) | 32.47 (15.03) | 1.01 (1.00) | 72.95 (16.83) | 68.04 (15.43) | 0.98 (0.96) |
| R.R. | 4.83 (27.09) | 4.61 (25.99) | 1.00 (1.01) | 60.88 (67.48) | 55.83 (62.15) | 0.97 (0.97) |
| W.J. | 38.50 (17.66) | 40.59 (16.67) | 1.00 (0.99) | 190.79 (33.53) | 172.97 (31.42) | 0.96 (9.99) |

The first figures in each column represent the data on the urine collected from 2-4 hr post ingestion.
The figures in parenthese represent the data on the urine collected from 12-24 hr post ingestion.
The metabolite is 2-ethylidene-1,5-dimethyl-3,3-diphenylpyrrolidine.

We claim:
1. A method for detecting unauthorized supplementation of a prescribed pharmacological dosage given to a patient, comprising the steps of:
   (a) providing a drug composition comprising a pharmacologically-active compound and a radiologically stable, isotopically distinct analogue having the same molecular structure as said compound and containing at least one radiologically-stable isotopic atom, said compound and said analogue being present in a first ratio by weight;
   (b) providing the patient with a prescribed dosage of the composition;
   (c) subsequently obtaining a physiological specimen of body fluid from the patient;

(d) subjecting the specimen to analysis to determine a first value indicative of the weight of a substance selected from the group consisting of said compound and its metabolites, and a second value indicative of the weight of a substance selected from the group consisting of said analogue and its corresponding metabolites; and (e) deriving from said first and second values a second ratio indicative of the ratio of the weight of said compound previously ingested by said patient and present in his metabolism to the weight of said analogue previously ingested by said patient and present in his metabolism; whereby said first ratio can be compared with said second ratio, so that any discrepancy between said first and second ratios indicative of unauthorized supplementation of dosage can be revealed.

2. A method as claimed in claim 1 in which the compound and the analogue are both isotopically labeled.

3. A method as claimed in claim 1 in which the drug composition comprises methadone mixed with a deuterated analogue of methadone.

4. A method as claimed in claim 3 wherein the deuterated analogue is 1,1,1-trideuterio methadone.

5. A method as claimed in claim 1 wherein said compound is selected from the group consisting of opiates, amphetamines, synthetic opiates, and barbiturates.

6. A method as claimed in claim 1 wherein said compound is selected from the group consisting of methadone, acetyl methadol, morphine, and heroin.

7. A method as claimed in claim 1 wherein step (d) comprises subjecting a gas chromatographic fraction of said specimen to repetitive mass spectrographic scan and comparing areas under the mass spectrographic curves representing cumulative ion currents for mass fragments that are indicative of the weight ratios of said compound and isotopic analogues thereof.

8. A method for detecting unauthorized usage of a pharmacologically-active chemical compound prescribed to a plurality of patients undergoing a course of therapy comprising:

(a) providing for said plurality of patients a corresponding plurality of mutually distinctively-labeled drug compositions, each said composition comprising said compound and at least one radiologically stable isotopically distinct analogue having the same molecular structure as said compound and containing at least one radiologically-stable isotopic atom and each composition being distinguished from each other composition by the presence of said radiologically stable isotopically distinct analogue (b) administering a prescribed dosage of said compositions to the patients, each patient receiving a different composition;

(c) obtaining a physiological specimen of a body fluid from a person suspected of receiving amounts of said compositions diverted from at least one patient in the group;

(d) subjecting said specimen to analysis to determine in said specimen values indicative of weights of substances selected from the group consisting of:
  (i) said compound and each isotopic analogue thereof; and
  (ii) metabolites of said compound and corresponding metabolites of said isotopic analogues; and (e) deriving from said values a weight ratio indicative of the relative amounts of said compound and of said analogues ingested by the person undergoing testing, whereby an indication of diversion of said compositions may be obtained.

9. A method as claimed in claim 8 wherein at least one of said compositions is distinguished from each other of said compositions by having a different weight ratio of said compound to said analogue.

10. A method as claimed in claim 8 wherein at least one of said compositions is distinguished from each other of said compositions by having a different number of isotopic atoms present in said analogue.

11. A method as claimed in claim 8 wherein at least one of said compositions is distinguished from each other of said compositions by having a different element isotopically replaced in said analogue.

12. A method as claimed in claim 8 wherein step (d) comprises subjecting a gas chromatographic fraction of said specimen to repetitive mass spectrographic scan and comparing areas under the mass spectrographic curves representing cumulative ion currents for mass fragments that are indicative of the weight ratios of said compound and isotopic analogues thereof.

13. A method as claimed in claim 8 wherein said compound, and each analogue thereof, is isotopically labeled.

14. A method as claimed in claim 8 wherein said compositions comprise methadone mixed with deuterated analogues of methadone.

15. A method as claimed in claim 14 wherein said deuterated analogues comprise mono-deuterated, di-deuterated and tri-deuterated methadone.

16. A method as claimed in claim 8 wherein said compound is selected from the group consisting of opiates, amphetamines, synthetic opiates, and barbiturates.

17. A method as claimed in claim 8 wherein said compound is selected from the group consisting of methadone, acetyl methadol, morphine, and heroin.

* * * * *